United States Patent
Lee et al.

(10) Patent No.: US 9,084,654 B2
(45) Date of Patent: Jul. 21, 2015

(54) INTERDENTAL CLEANING MEMBER AND MANUFACTURING METHOD THEREOF

(75) Inventors: Kyung-Sub Lee, Chungcheongnam-do (KR); Sung-Jin Kim, Daejeon (KR); Jae-Hyun Ahn, Daejeon (KR); Sug-Youn Chang, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 109 days.

(21) Appl. No.: 13/695,594

(22) PCT Filed: May 2, 2011

(86) PCT No.: PCT/KR2011/003260
§ 371 (c)(1),
(2), (4) Date: Apr. 16, 2013

(87) PCT Pub. No.: WO2011/136626
PCT Pub. Date: Mar. 11, 2011

(65) Prior Publication Data
US 2013/0198987 A1    Aug. 8, 2013

(30) Foreign Application Priority Data
Apr. 30, 2010  (KR) .................. 10-2010-0040771

(51) Int. Cl.
*A46D 1/00*   (2006.01)
*A61C 15/00*   (2006.01)
*A61C 15/02*   (2006.01)
*A46D 3/00*   (2006.01)

(52) U.S. Cl.
CPC . *A61C 15/00* (2013.01); *A46D 1/00* (2013.01); *A46D 3/00* (2013.01); *A61C 15/02* (2013.01); *A46B 2200/108* (2013.01)

(58) Field of Classification Search
CPC ............. A61C 15/00; A46D 1/00; A46D 3/00
USPC .................................. 15/207.2, 167.1; 300/21
See application file for complete search history.

(56) References Cited

U.S. PATENT DOCUMENTS

| | | | |
|---|---|---|---|
| 3,837,351 A | 9/1974 | Thornton | |
| 3,896,824 A | 7/1975 | Thornton | |
| 6,090,488 A | 7/2000 | Kweon | |
| 6,158,444 A | 12/2000 | Weihrauch | |
| 6,872,449 B2 * | 3/2005 | Weihrauch et al. | ........... 428/370 |
| 7,644,466 B2 | 1/2010 | Weihrauch et al. | |

FOREIGN PATENT DOCUMENTS

| | | |
|---|---|---|
| CN | 101695415 A * | 4/2010 |
| EP | 0707836 A2 | 4/1996 |
| JP | 2001-245904 A | 9/2001 |
| JP | 2003-245133 A | 9/2003 |
| JP | 2004-208816 A | 7/2004 |
| JP | 2004-298328 A | 10/2004 |
| JP | 2006-158842 A | 6/2006 |
| JP | 2007-159727 A | 6/2007 |

(Continued)

*Primary Examiner* — Shay Karls
(74) *Attorney, Agent, or Firm* — McDermott Will & Emery LLP

(57) ABSTRACT

The present disclosure relates to an interdental cleaning member and a manufacturing method thereof, and more particularly, to an interdental cleaning member and a manufacturing method thereof, which may easily remove food residues between teeth without damaging the gums.

3 Claims, 4 Drawing Sheets

(56) References Cited

FOREIGN PATENT DOCUMENTS

| | | | |
|---|---|---|---|
| JP | 2009142481 A | * | 7/2009 |
| WO | 98/00049 | A1 | 1/1998 |
| WO | 00/71788 | A1 | 11/2000 |
| WO | 02/074184 | A1 | 9/2002 |
| WO | 2009/097600 | A1 | 8/2009 |

* cited by examiner (a)

(b)

INTERDENTAL CLEANING MEMBER AND MANUFACTURING METHOD THEREOF

CROSS-REFERENCE TO RELATED APPLICATION

The present application is a national phase entry of International Application No. PCT/KR2011/003260 filed on May 2, 2011, which claims priority to Korean Patent Application No. 10-2010-0040771 filed in the Republic of Korea on Apr. 30, 2010, the disclosures of which are incorporated herein by reference.

TECHNICAL FIELD

The present disclosure relates to an interdental cleaning member and a manufacturing method thereof, and more particularly, to an interdental cleaning member and a manufacturing method thereof, which may easily remove food residues between teeth without damaging the gums.

BACKGROUND ART

Usually, in order to remove impurities between teeth which cannot be easily cleaned by a general tooth brush after a person eats food, a toothpick having one or two sharp ends or an interdental toothbrush is used. In other words, a toothpick and an interdental toothbrush may be used to prevent tooth decay and periodontal diseases in advance.

In more detail, a toothpick is made of wood, plastic, starch or the like and used for removing food residues between teeth. However, if a gap between teeth is small, the sharp end of the toothpick may not easily insert between the teeth and may not remove all food residues. In addition, the hard and sharp tip of a toothpick is prone to breaking, which greatly inconveniences a user.

In order to solve these problems, an interdental toothbrush having a brush mounted thereto has been manufactured and used. As shown in FIG. 1, an interdental toothbrush 10 includes a grip portion 11 easily gripped by a user, a brush portion 12 formed at one end of the grip portion 11, and a cover 15 for protecting the brush portion 12.

The brush portion 12 includes a wire unit 13 formed by two wires and a brush 14 having bristles formed at regular intervals in the longitudinal direction of the wire unit 13. In other words, as the wire unit 13 moves into and out of a gap between teeth, the brush 14 removes food residues.

However, the interdental toothbrush 10 having the brush 14 mounted thereto as described above has no market competition due to a high production cost caused by planting bristles of the brush 14 to the wire unit 13, and the metallic feeling of the wire gives a user an unpleasant feeling, which adds to the inconvenience.

In addition, since the wire unit 13 is produced by twisting thick wires, the wire unit 13 may not easily insert between teeth, making it difficult to properly clean the teeth.

Moreover, the hardness of the wires may frequently damage the gums.

Such a conventional toothpick and interdental toothbrush may not easily remove impurities between teeth. In addition, such conventional toothpick and interdental toothbrush may damage the gums, which may be a cause for disease, and may also cause tooth decay or cavities, damaging the structure of teeth in the long run.

Additionally, to injection-mold a toothpick to form a brush at an end of the toothpick by using the same material for both the brush and the toothpick, it is impossible to minutely form a plurality of bristles of the brush simultaneously at an end of the toothpick, and therefore, difficult to implement the features of the interdental toothbrush.

DISCLOSURE

Technical Problem

The present disclosure is designed to solve the problems of the prior art, and therefore it is an object of the present disclosure to provide an interdental cleaning member and a manufacturing method thereof, which may easily remove impurities such as food residues between teeth while minimizing irritation applied to the gums.

Technical Solution

In an aspect of the present disclosure, there is provided an interdental cleaning member for removing impurities between teeth, which includes a bristle made of a yarn to have a length of 1 cm to 15 cm, wherein the bristle has a bending restoration rate of 10% to 80% and is formed to have a tapered shape in at least a front portion of the bristle along the longitudinal direction of the bristle so that the bristle has a diameter of 0.001 mm to 2 mm at a distance of about 0.1 mm from the front end of the tapered portion.

According to the present disclosure, the yarn preferably has a diameter of 0.5 mm to 3 mm, and the yarn is preferably formed to have an uneven shape or a wave shape.

Preferably, the tapered portion has a curved portion with an irregular inclined surface.

Meanwhile, the yarn may be made of any one of nylon-based and polyester-based materials, a functional substance may be selectively added to the material of the yarn, and the functional substance may be an inorganic substance of calcium carbonate or silica.

In addition, a component layer containing a functional component is preferably formed at the bristle, and the functional component preferably includes at least one of fluorine components, antimicrobial components, fragrance components, and pigment components.

In another aspect of the present disclosure, there is also provided a manufacturing method of an interdental cleaning member, which includes (a) stretching a yarn by spinning; (b) tapering a bristle, formed by cutting the yarn to have a length of 1 cm to 15 cm, along the longitudinal direction of the bristle so that the bristle has a tapered shape in at least a front portion thereof; and (c) washing and drying the bristle, wherein the bristle has a bending restoration rate of 10% to 80% and has a diameter of 0.001 mm to 2 mm at a distance of about 0.1 mm from the front end of the tapered portion formed by the step (b).

According to the present disclosure, in the step (b), a tapering process of soaking a bristle in a strong alkali solution or a strong acid solution and a tapering process using a grinding process with a grinder may be selectively performed or subsequently performed so that a curved portion with an irregular surface is formed at the tapered portion.

Meanwhile, in the step (a), the yarn may be made of any one of nylon-based and polyester-based materials, a functional substance may be selectively added to the material of the yarn when the yarn is made, and the functional substance may be an inorganic substance of calcium carbonate or silica.

In addition, after the step (b), the manufacturing method may further include forming a component layer by dipping the bristle in a solution containing a functional component, and the functional component preferably includes at least one of fluorine components, antimicrobial components, fragrance components, and pigment components.

DESCRIPTION OF DRAWINGS

Other objects and aspects of the present disclosure will become apparent from the following descriptions of the embodiments with reference to the accompanying drawings in which.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the spirit and scope of the disclosure.

Figure 1:
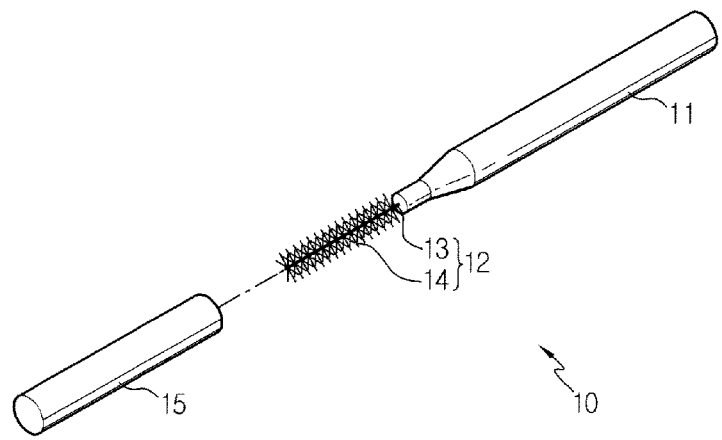
FIG. 1 is a perspective view showing a conventional interdental toothbrush.
Figure 2:
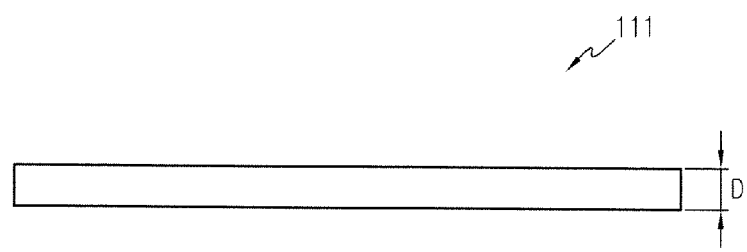
FIG. 2 is a side view showing a yarn of an interdental cleaning member according to a preferred embodiment of the present disclosure.
Figure 3:
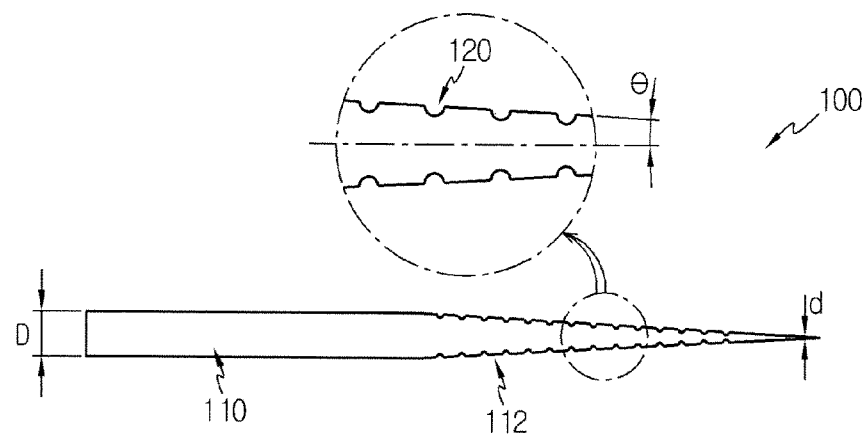
FIG. 3 is a side view showing an interdental cleaning member according to a preferred embodiment of the present disclosure.

FIG. 2 is a side view showing a yarn of an interdental cleaning member according to a preferred embodiment of the present disclosure, and FIG. 3 is a side view showing an interdental cleaning member according to a preferred embodiment of the present disclosure.

Referring to FIGS. 2 and 3, an interdental cleaning member 100 includes a bristle 110 made by a stretched yarn which gives it a predetermined length and a predetermined diameter.

The bristle 110 has a tapered shape in at least a front end of the bristle 110 along the longitudinal direction of the bristle 110 and also has a bending restoration rate of 10% to 80%. At this time, the yarn 111 represents a state of being spun and stretched, and the bristle 110 represents a state in which a tapering process described later is performed to the yarn 111 to have a tapered shape.

Figure 4:
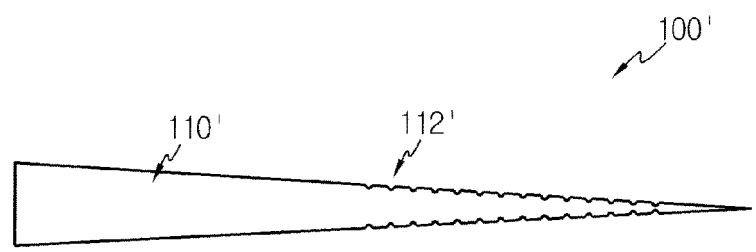
FIG. 4 is a side view showing an interdental cleaning member according to another preferred embodiment of the present disclosure.

In other words, the yarn 111 is formed by spinning as shown in FIG. 2, and the bristle 110 is formed to have a tapered shape as shown in FIG. 3. At this time, the bristle 110 may have a tapered shape at a partial portion of the front end as shown in FIG. 3, and the bristle 110' may also have a tapered shape over the entire configuration as shown in FIG. 4. Hereinafter, the tapered portions of such bristles 110, 110' will be referred to as tapered portions 112, 112', respectively.

Referring to FIGS. 2 and 3 again, the bristle 110 is formed by cutting the stretched yarn 111 and then performing a tapering process thereto as described above. The tapering process will be described below.

The bristle 110 according to the present disclosure is made of any one of nylon-based and polyester-based materials. The polyester-based material is preferably selected from PET (polyethylene terephthalate), PBT (polybutylene terephthalate), and PTT (polytrimethylene terephthalate).

Additionally, the yarn 111 may also be made by further adding a functional substance to the above material. The functional substance is preferably an inorganic substance of calcium carbonate or silica. The addition of the functional substance is to facilitate roughness to the surface of the tapered portion when a tapering process described below is performed.

The yarn 111 made by spinning the above material is stretched to have suitable elasticity and flexibility. In other words, the bristle 110 has a bending restoration rate of 10% to 80% due to the characteristic of its material and owing to the stretching process.

In relation to the numerical range of the bending restoration rate, if the bending restoration rate is less than 10%, the yarn 111 may be too hard and inflexible which may irritate and damage the gums when removing impurities between teeth. If the bending restoration rate is greater than 80%, the yarn 111 may be too soft to be able to transfer the force, and so the yarn 111 may not easily insert between teeth.

After being stretched, the yarn 111 is cut to have a diameter D of 0.5 mm to 3 mm and a length of 1 cm to 15 cm. At this time, the yarn 111 preferably has a length of 2 cm to 15 cm. More preferably, the yarn 111 is cut to have a length of 3 cm to 15 cm.

In addition, the stretched yarn 111 more preferably has a diameter D of 0.5 mm to 2 mm. The diameter D (thickness) of the yarn 111 as described above corresponds to a thickness required for the user to easily grip the interdental cleaning member 100. Meanwhile, since the bristle 110 is made of the yarn 111, the diameter D of the yarn 111 may be interpreted as the diameter D of the bristle 110.

In relation to the numerical range of the diameter D of the yarn 111, if the yarn 111 has a diameter D greater than 3 mm, the nylon-based or polyester-based material of the yarn 111 may not be easily spun and stretched due to its properties, and it is not easy to obtain a desired shape and desired properties in a following tapering process. If the yarn 111 has a diameter D less than 0.5 mm, the stretched yarn 111 is too thin to be gripped by the user, and the yarn 111 becomes too soft to be able to transfer the force, so the yarn 111 is not appropriate for cleaning teeth.

In addition, in relation to the length of the bristle 110, if the bristle 111 has a length greater than 15 cm, the length of the bristle 110 is unnecessarily long and so the material is wasted. If the bristle 110 has a length less than 1 cm, since the length of the bristle 110 is too short, the bristle is not easily gripped by the hand, which inconveniences the user.

According to the present disclosure, the tapered portion 112 is formed by a chemical process and/or a mechanical process. At this time, the tapered portion 112 formed by a tapering process has a diameter D of 0.001 mm to 2 mm at a distance of about 0.1 mm from the front end of the bristle 110.

This diameter D gives a thickness which allows the interdental cleaning member 100 to easily insert between teeth.

Meanwhile, the tapered portion 112 may also have a length of 1 cm to 15 cm. In other words, by having the length, the tapered portion 112 may be formed at the entire or partial portion of the bristle 110. For example, in the case the tapered portion 112' is formed over the entire portion of the bristle 110' as shown in FIG. 4, the interdental cleaning member 100' may have a tapered shape as a whole.

A tilt angle θ of the tapered portion 112, 112' is 0.3° to 12° from the center of the bristle 110.

In relation to the numerical range of the tilt angle θ, a tilt angle θ less than 0.3 is not desirable since the tapered portion 112, 112' should have a length greater than 15 cm which undesirably demands a great amount of time for the tapering process. In addition, if the tilt angle θ is greater than 12°, the tapered length decreases in comparison to the length of the demanded tapered portion 112, 112', and so the member may not be used as an interdental cleaning instrument.

Meanwhile, a curved portion 120 having various uneven patterns is formed at an inclined surface of the tapered portion 112, 112'. In other words, the inclined surface has an irregular surface with an uneven design or the like. Therefore, the interdental cleaning effect is improved.

Additionally, even though the yarn 111 of the interdental cleaning member 100, 100' has been illustrated as being stretched by spinning to have a section with a cylindrical shape, the yarn 11 may be configured to have a section with various shapes such as an oval shape, without being limited to the above.

Figure 5:
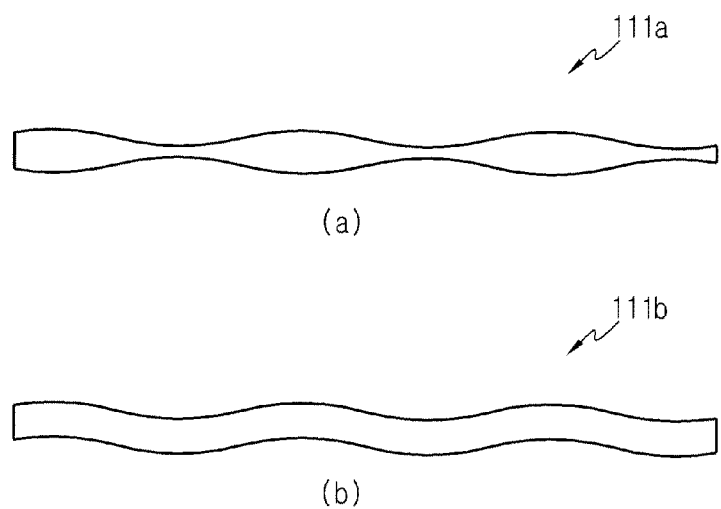
FIG. 5 is a diagram showing a yarn of an interdental cleaning member according to another preferred embodiment of the present disclosure.

For example, as shown in FIG. 5, the yarn 111a, 111b may be formed to have an uneven shape or a wave shape. In other words, while stretching the material after spinning, a yarn may be extracted with various shapes according to a stretching speed in comparison to a spinning speed or a hole through which the spun material passes. In addition, by stretching, the yarn may have a section with a circular or oval shape, and the yarn may also have various shapes by means of spinning through a hole with a circular or polygonal shape. If the yarn is formed to have various shapes, the yarn may be easily gripped by the user.

Figure 6:
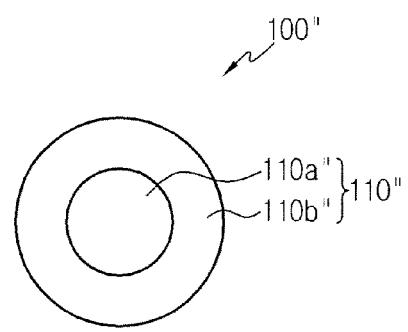
FIG. 6 is a front sectional view showing an interdental cleaning member according to still another preferred embodiment of the present disclosure.

Meanwhile, even though the bristle 110, 110' has been illustrated as having a single layer due to the spinning of the yarn 111, a component layer containing a functional component may be further formed at the bristle 110, 110'. For example, as shown in FIG. 6, the bristle 110" includes a center portion 110a" made of a yarn and a component layer 110b" containing a functional component. At this time, the center portion 110a" has the same material and shape as the yarn 111 described above, and the component layer 110b" includes at least one of fluorine components, antimicrobial components, fragrance components, and pigment components.

The component layer 110b" may be formed by dipping at least a front end of the bristle 110" in a solution containing a functional component along the longitudinal direction of the bristle 110" or coating the center portion 110a" with a functional component. In addition, the component layer 110b" may also be performed by performing double-spinning when the yarn is obtained by spinning.

By the formation of the component layer 110b" as described above, not only can this improve the health of the teeth and the gums, but also enhance the feeling in use, and improve the appearance of the cleaning member.

Now, a manufacturing method of the interdental cleaning member 100 as above will be described in detail.

Figure 7:
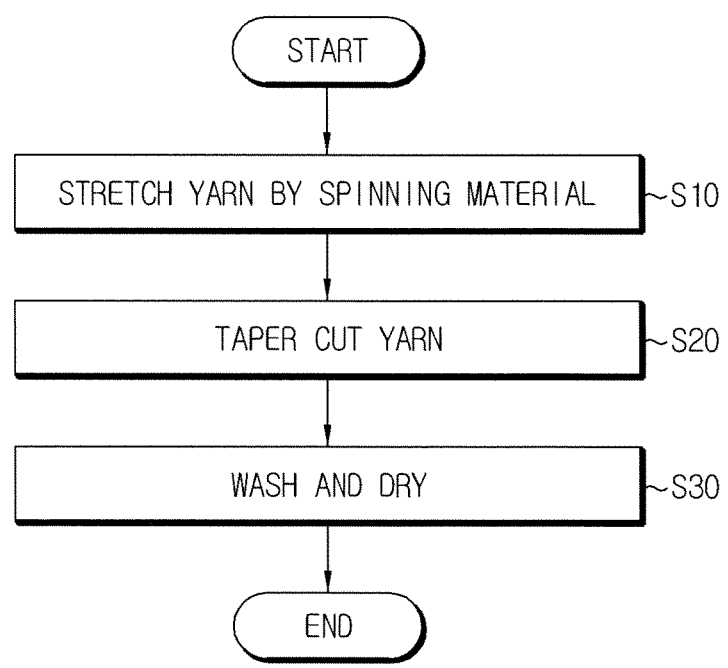
FIG. 7 is a flowchart for illustrating a manufacturing method of an interdental cleaning member according to a preferred embodiment of the present disclosure.

FIG. 7 is a flowchart for illustrating a manufacturing method of an interdental cleaning member.

First, a yarn 111 is made by spinning any one of nylon-based and polyester-based materials (S10). At this time, a process of stretching the yarn 111 is preferably performed together with the spinning.

The yarn 111 is formed to have a diameter of 0.5 mm to 3 mm through the stretching process and is then cut into a predetermined length. For example, the predetermined length is 1 cm to 15 cm.

Subsequently, the cut yarn 111 is tapered (S20). At this time, the tapering process may be performed in a chemical way or in a mechanical way.

First, among the processes for forming the tapered portion 112 at the yarn 111, a chemical process will be described first.

The cut yarn 111 is vertically soaked in a solution containing strong alkali or strong acid. At this time, the yarn 111 is soaked as much as the length where the tapered portion 112 is to be formed. In other words, the strong alkali or strong acid tapers the soaked yarn 111 at a certain temperature and concentration. In the tapering process, the tapered portion is formed as the bristle is slowly decomposed by the solution.

Meanwhile, if only a tip of the bristle is dipped in the solution, the solution climbs along the surface of the bristle due to the capillary phenomenon. In other words, the tapered portion is formed at the bristle as the tapering process is performed to the bristle with different periods according to the length of the bristle.

At this time, the tapering process may not only form the tapered portion 112 but also form a curved portion 120 at the tapered portion 112. At this time, in order to form the curved portion 120 more easily, a functional substance may be added to the material of the yarn 111. For example, an inorganic substance such as calcium carbonate and silica, which is a functional substance, is added to the material of the yarn 111, and the material is spun to obtain the yarn 111. After that, if the yarn 111 is soaked in a strong alkali or acid solution, a chemical reaction is performed to form the curved portion 120 having a surface with a diameter of 0.01 μm to 0.1 mm. In other words, the curved portion may be easily formed by using a chemical reaction according to the characteristics of the material.

If the tapering process using a chemical way is performed, an inclined flat surface or an irregular uneven surface is formed at the yarn 111 due to the capillary phenomenon during the tapering process.

If the tapering process is complete, a process of neutralizing the yarn 111 by using a caustic soda or potassium hydroxide solution and then washing the yarn 111 with water (S30) is performed. If the drying process is complete, the interdental cleaning member 100 is completely manufactured.

Next, among the processes for forming the tapered portion 112 at the yarn 111, a mechanical process will be described.

The cut yarn 111 is tapered by being ground with a grinder (not shown). In other words, the yarn 111 is ground to have a tapered shape at a partial region or the entire region thereof. This grinding process may allow the bristle 110 to have a tapered shape similar to the chemical tapering process.

If the tapering process is complete, the bristle 110 is washed and dried to completely manufacture the interdental cleaning member.

Meanwhile, the tapered portion 112 made by the mechanical process has a shorter length than that by the chemical process and so the bristle 110 is less soft. However, since the tapered surface is formed irregularly, the cleaning effect is improved.

Therefore, when the tapered portion 112 is formed by means of mechanical grinding, it is possible to primarily perform a chemical tapering process to make a certain shape and then secondarily perform a mechanical grinding process so that the bristle 110 has an irregular surface. In this case, the bristle 110 may have a longer tapered portion in comparison to the case where only the mechanical processing is performed, and so it is possible to enhance elasticity and flexibility of the bristle 110.

Meanwhile, by using the tapering process as described above, a tilt angle θ of the tapered portion 112 may be selectively adjusted. In other words, the tapering process is performed so that the tapered portion 112 has a tilt angle θ of 0.3° to 12° based on the center of the bristle 110 in the longitudinal direction.

If the yarn 111 is tapered to have a certain thickness and shape as described above, the interdental cleaning member 100 may have suitable elasticity and flexibility together and may also easily insert into a border of teeth and the gums to easily clean impurities such as food residues therefrom.

Meanwhile, when the yarn 111 is spun and stretched, the yarn may have various shapes (see 111a and 111b of FIG. 5) by adjusting a spinning rate, a stretching rate and a diameter of the hole through which the material of the yarn 111 passes, and the interdental cleaning member 100 may be manufactured by using such a yarn 111, 111a, 111b.

In addition, in order to help the health of the gums and teeth and enhance the feeling in use, the component layer (see 110b" of FIG. 6) containing a functional component may be formed at the yarn 111 when the interdental cleaning member is manufactured. The component layer 110b" is formed by dipping the bristle in a solution containing the functional component. The component layer 110b" includes at least one of fluorine components, antimicrobial components, fragrance components, and pigment components. At this time, the step of forming the component layer 110b" is preferably performed after the tapering process is complete.

The bristle prepared as described above has a bending restoration rate of 10% to 80%. In other words, the bending restoration rate of the bristle is measured according to the test based on KS Standards (KS G 3103: 2003).

The present disclosure has been described in detail. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

INDUSTRIAL APPLICABILITY

The interdental cleaning member and a manufacturing method thereof according to the present disclosure gives the following effects.

First, since a yarn is stretched by means of spinning, the interdental cleaning member has excellent elasticity and flexibility in spite of great thickness.

Second, the tapered portion formed by a tapering process is soft and flexible, and so the interdental cleaning member is not easily broken.

Third, since the front end of the tapered portion is very thin, it may easily insert between teeth or between a tooth and the gums.

Fourth, since the curved portion with an irregular surface is formed at the tapered portion, the cleaning effect of the interdental cleaning member is improved.

Fifth, since the interdental cleaning member may be easily produced, a production cost may be reduced.

Sixth, since the interdental cleaning member may easily insert between teeth and have elastic and flexible properties, the interdental cleaning member may implement the effects of an interdental toothbrush or floss.

What is claimed is:

1. A manufacturing method of an interdental cleaning member, comprising:
    (a) stretching a yarn by spinning to have a diameter of 0.5 mm to 3 mm;
    (b) cutting the yarn to have a length of 1 cm to 15 cm to form a bristle;
    (c) tapering the bristle to have a tapered portion along a longitudinal direction of the bristle so that the bristle has a tapered shape in at least a front portion thereof; and
    (d) washing and drying the bristle,
    wherein the bristle has a bending restoration rate of 10% to 80%, the tapered portion has a diameter of 0.001 mm to 2 mm at a distance of about 0.1 mm from a front end of the bristle, and the tapered portion has a tilt angle of 0.3° to 12° based on a center of the bristle, and
    wherein, in step (c), the tapered portion has a curved portion with an irregular surface formed thereon by primary tapering in which the bristle is soaked in a strong alkali solution or a strong acid solution and then by secondary tapering in which the bristle is grinded with a grinder.

2. The manufacturing method of an interdental cleaning member according to claim 1,
    wherein, in step (a), the yarn is made of any one of nylon-based and polyester-based materials,
    wherein a functional substance is selectively added to the material of the yarn when the yarn is made, and
    wherein the functional substance is an inorganic substance of calcium carbonate or silica.

3. The manufacturing method of an interdental cleaning member according to claim 1, after step (c), further comprising:
    forming a component layer by dipping the bristle in a solution containing a functional component,
    wherein the functional component includes at least one of fluorine components, antimicrobial components, fragrance components, and pigment components.

* * * * *